(12) United States Patent
Radermacher et al.

(10) Patent No.: US 8,308,730 B2
(45) Date of Patent: Nov. 13, 2012

(54) METHOD OF AND APPARATUS FOR DETERMINING THE MECHANICAL AXIS OF A FEMUR

(75) Inventors: Klaus Radermacher, Stolberg (DE); Robert Elfring, Aachen (DE)

(73) Assignee: Rheinisch-Westfaelisch-Technische Hochschule Aachen, Aachen (DE)

( * ) Notice: Subject to any disclaimer, the term of this patent is extended or adjusted under 35 U.S.C. 154(b) by 434 days.

(21) Appl. No.: 12/601,660

(22) PCT Filed: May 21, 2008

(86) PCT No.: PCT/EP2008/004056
§ 371 (c)(1),
(2), (4) Date: Dec. 29, 2009

(87) PCT Pub. No.: WO2008/145287
PCT Pub. Date: Dec. 4, 2008

(65) Prior Publication Data
US 2010/0174327 A1 Jul. 8, 2010

(30) Foreign Application Priority Data

May 25, 2007 (DE) .......................... 10 2007 024 708

(51) Int. Cl.
*A61B 17/58* (2006.01)
*A61B 17/60* (2006.01)
*A61F 2/00* (2006.01)

(52) U.S. Cl. ......................................... 606/89; 606/102
(58) Field of Classification Search ................ 606/86 R, 606/88–89, 102
See application file for complete search history.

(56) References Cited

U.S. PATENT DOCUMENTS 5,520,694 A 5/1996 Dance et al. .................... 606/86
5,690,638 A 11/1997 Dance et al. .................... 606/88

*Primary Examiner* — Andrew Yang
(74) *Attorney, Agent, or Firm* — Andrew Wilford

(57) ABSTRACT

The invention relates to a device for determining the mechanical leg axis of a femur. Said device is provided with a shaft (3) that comprises, on one of its ends, a securing device (5) that is connected to the shaft and that can be blocked at various angles, in order to obtain a fastening that can be blocked in an angle stable manner and that fastens the shaft (3) to the knee joint of a femur, and comprises a gripping element (10) on its other end. A force-torque measuring device (14) is arranged between the gripping element (10) and the shaft (3), said device enabling the longitudinal and/or transversal force components of force (Fz) exerted via the shaft (3) upon the knee joint to be measured by means of the gripping element (10) and/or torque produced thereby. The invention also relates to a method for determining the mechanical leg axis of a femur by means of the above mentioned device. The shaft (3) is fixed in its position by blocking at various angles, in particular an articulated connection when the measured transversal force components or torque produced thereby is minimized, in particular, is zero.

19 Claims, 3 Drawing Sheets

METHOD OF AND APPARATUS FOR DETERMINING THE MECHANICAL AXIS OF A FEMUR

CROSS REFERENCE TO RELATED APPLICATIONS

Figure 1:
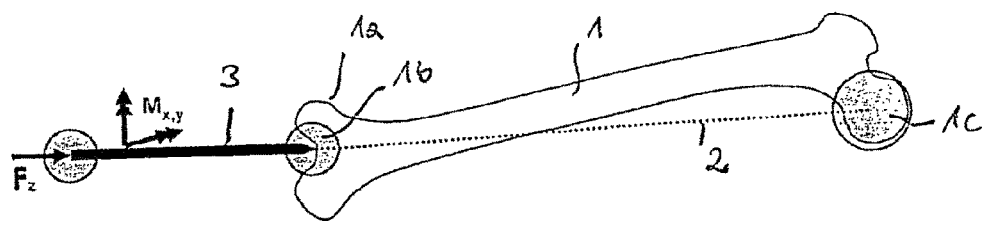

This application is the US national phase of PCT application PCT/EP2008/004056, filed 21 May 2008, published 4 Dec. 2009 as WO2008/145287, and claiming the priority of German patent application 102007024708.9 itself filed 25 May 2007, whose entire disclosures are herewith incorporated by reference.

The invention relates to a method of and apparatus for determining the mechanical axis of a femur.

In the field of knee endoprostheses, an acknowledged problem is that the knee prosthesis must be correctly positioned on the mechanical support line of the leg, i.e. on the mechanical axis, the so-called Mikulicz line. This mechanical axis runs through the center of the ankle joint, the center of the knee joint, and the center of the head of the femur.

During surgery there is the problem that the center of the head of the femur cannot be determined with no further information. However, this is of crucial importance for correctly positioning the femoral components of a knee prosthesis. Only straight-line positioning results in an unstable position of equilibrium that can be stabilized by ligaments and muscle structures. Deviations from this ideal straight-line positioning can lead to excess loads, however, especially in the knee joint prosthesis, so that the result can be a significant reduction in the service life of an artificial knee joint.

For approximately correctly positioning the femoral components of a knee prosthesis, in the prior art it is acknowledged as a standard for instance to introduce an intramedullary pin into the femoral medullary canal of the femur. A prosthesis can then be positioned relative to this pin at an angle determined in advance in an x-ray image, this angle being provided in order to take into account the deviation of the actual mechanical axis from the orientation of the medullary canal. However, such a method is extremely invasive and involves a high risk of embolism due to compression of the bone marrow when the pin is driven in.

It is also known to perform knee surgeries using navigation systems, which lead to better results but which require a great deal of complexity due to the use of plotting software and the need for positioning and tracking systems.

The object of the invention is to provide an apparatus and a method with which the mechanical axis of a femur can be determined with sufficient accuracy to be able in subsequent surgery to fit a knee prosthesis using the mechanical axis thus found and established. It is furthermore the object of the invention to provide an apparatus and a method that can be used or applied in preparation for a knee surgery.

This object is inventively attained using an apparatus for determining the mechanical axis of a femur, which apparatus has a shaft having has at its one end a mount that can be locked in position and that is connected in an angle-variable manner to the shaft for securing the shaft to the knee joint of a femur in an angularly fixed, lockable manner and at its other end is provided with a handgrip, a force/torque sensor being provided between the handgrip and the shaft that can measure longitudinal and/or transverse force components of a force exerted on a knee joint and/or measure torque generated thereby by means of the handgrip via the shaft.

According to the invention at least the resultant transverse forces or torques generated thereby are measured, preferably also the force exerted axially of the shaft.

Thus it is possible in accordance with the invention to carry out a method for determining the mechanical axis of a femur, whereby such a shaft that is connected at its one end such that it can be locked in position and is angle-variable to a mount, is secured to the distal end of a femur, especially at the knee joint, and then a force is exerted on the distal end via the shaft.

It can preferably be provided that the angularly fixed connection, which can be locked in position, between the shaft and the mount is formed as at least one lockable joint, in particular a lockable ball-and-socket joint.

The result, due to the angle-variable, especially swiveling connection between the mount and the shaft, is a system with two joints, specifically resulting from the hip joint and the joint or the angle-variable arrangement in the mount so that a force that is exerted on the distal end of the femur resolves into force components transverse to the direction of the exerted force if the direction of the exerted force is not exactly aligned with the mechanical axis.

Such transverse forces then generate torques that can be measured by means of the above-described force/torque sensor. These torques act at a distance from the location at which the force is introduced (mount at the distal bone end) and can therefore be detected with the force/torque sensor between the grip and the shaft. They act especially in the segment of the force/torque sensor between grip and shaft.

The force break-up either does not occur or transverse forces and torques generated thereby are minimized or ideally equal to zero only if the force line of the force exerted runs precisely through both joints, i.e. the force exerted is exactly aligned with the mechanical axis. In this manner one can be sure that at the instant in which the measured transverse components are minimized, and especially when they equal zero, the shaft with which the force is exerted on the distal end of the femur is also precisely positioned with respect to the mechanical axis, the so-called Mikulicz line.

In this embodiment, even if the discussion centers on determining the mechanical axis, the apparatus and the method can analogously be employed for determining other load axes, such as for example in the tibia-ankle joint. The invention is not limited to determining the leg axis.

Thus it is inventively provided that when this condition is satisfied the shaft is fixed in position by locking the angle-variable, especially swiveling, connection between the shaft and the mount. The fixed shaft then has a longitudinal extension that coincides with the mechanical axis or has a known predefined position, especially such that a corresponding apparatus can reproduce the longitudinal axis.

Such locking in position can occur for example by fixing the swivel joint, for example the ball-and-socket joint. Fixing can also alternatively occur such that a corresponding reference is fixed on the leg, which reference defines the longitudinal axis or has a defined known positional relationship thereto, for example by adding Kirschner wires, a "bear claw," or the like.

In order to do this, according to the invention the force components or torques generated thereby are recorded by means of a force/torque sensor that is provided directly on the shaft and via which a force, in particular a force axial to the shaft, is exerted on the shaft.

For instance the transverse forces that occur when the force is exerted and/or torques generated by the transverse forces are detected by means of the force/torque sensor. In one embodiment they can be detected for example electronically qualitatively and/or quantitatively and can be transmitted to a display, for instance to a monitor or some other display. In another embodiment, the forces or torques can be measured purely mechanically and shown on a display, for example an indicator display.

This is particularly convenient because changing force and torque variables such as for example the magnitude and orientation of the transverse force components or torques are visible directly on the display and, due to the angle-variable, in particular swiveling, connection to the mount, the direction of the force introduced via the shaft can be changed until the transverse force components/torques disappear.

To this end, it is advantageously provided that an inventive apparatus for carrying out such a method has a handgrip that can manually exert the forces via the shaft on the femur. Using the handgrip, the position of the entire apparatus can be modified relative to the distal end of the femur and in this case in particular to the mount due to the angle-variable, especially swiveling, connection thereto.

In the inventive method and apparatus it can furthermore be provided that the amount of force exerted can be shown on a display, especially relative to a minimum force. This is preferred because only when a certain minimum force is exerted do transverse components and torques of adequate magnitude occur with an incorrect position that are suitable for displaying and correcting the incorrect orientation. For instance, the display of an adequate force can be shown by a color change in a display, for example from red to green. In this case, the color change to green is a visual indicator that the necessary minimum force has been attained. The greater this force is selected to be, especially within reasonable limits, the greater the accuracy of the positioning due to correspondingly pronounced transverse forces and/or torques.

The transverse force components or the torques generated thereby can be shown on a display for instance as cross-hairs or a relative position to a center in the display. This is especially advantageous when a Cartesian coordinate system is the basis for it and for instance the direction of the force exerted is assumed as the Z direction, it then being possible to detect transverse force components in the X and Y directions using the measuring apparatus. Thus the magnitude of the transverse force components and/or torques can be shown relative to the origin by the position of cross-hairs in a Cartesian coordinate system.

Thus, at the moment at which the cross-hairs are at the origin one is assured that the transverse force components and torques are minimized, and ideally are equal to zero, and thus the shaft that which in this position is exerting the force on the distal end of the femur is in the ideal position, i.e. is an extension of the Mikulicz line. The above-described change in color is shown directly using the coloring of the cross-hairs.

A display can also be realized in any other desired display apparatus, for example a display that is mounted directly on the apparatus, for example on the handgrip. This display can also be purely mechanical using corresponding measuring devices, in particular with mechanical indicators. In this case where necessary it may only be possible to display the direction in which the operator must move the grip in order to reach the ideal position.

In order to avoid false measurements that could result because the distal end of the femur possibly causes a force component or torque to be shown in the display due to the force of gravity, the method according to the invention prior to carrying out the actual measurement for determining the leg axis the active weight is determined using the force/torque sensor and then is taken into account in subsequent measurements. In this way the actual weight can be compensated for.

One inventive apparatus for carrying out this method has a shaft as described above that at its one end is connected to the distal end of a femur via an angle-variable, especially swiveling, connection that is formed by a mount. Thus the force described above can be exerted on the distal end via a handgrip at the other end of the shaft.

In this case it is considered advantageous for the force/torque sensor to be arranged between the handgrip and the shaft. For instance, such an arrangement can be configured to be detachable when the force/torque sensor is arranged for instance between two flanges. One of the two flanges can be associated with the handgrip and the other with the shaft.

In one preferred embodiment of the inventive apparatus the shaft is formed in at least two parts and especially can telescope. One part of the shaft can be connected to the mount as described above in a manner such that it can be locked in position in an angle-variable manner, especially swiveling, another part having the gripping apparatus and the force/torque sensor and both parts being detachably connectable to one another. The ability to telescope can be realized in the two parts being detachably connected to one another. The ability to telescope in this case has the special advantage that the length of the entire apparatus and in particular the length of the shaft can be adapted to the prevailing conditions or to operator preferences.

Making the shaft in at least two parts has the advantage that the connection between these two parts can be released so that after the shaft has been locked in position in the mount in an angularly fixed manner the rest of the inventive apparatus can be removed from the piece of the shaft that is locked in position. The shaft end thus locked in position and secured to the distal end of the femur in an angularly fixed manner can then be employed to fit a knee prosthesis to the distal end of the femur in a subsequent surgery. This can occur especially in the known manner.

In another preferred refinement, the shaft is formed with bends upstream of the mount, that is especially the above-described part that is connected to the mount, in particular such that a front part and a rear part of the shaft (upstream and downstream of the bend/turn) are in a line. The shape of the bend or where necessary multiple bends can occur such that the shaft fits around an obstacle, for example a kneecap, in the region of the bend/turn. Thus such an apparatus can preferably also be employed in a minimally invasive manner.

In order to create the above-described ability of the angle-variable, especially swiveling, connection between shaft and mount to be locked in position, in one particularly preferred embodiment the shaft is tubular, at least in part, a locking apparatus for locking in position the angle-variable, especially swiveling, connection to the mount being detachable and/or fixable through the tubular shaft. This can occur for instance in that a pin, especially a multipart pin, that is provided in the tubular shaft and can serve to actuate the locking apparatus in the mount.

In this case the pin can be actuated by an actuating element that is provided on the handgrip. This has the special advantage that an operator can exert the force onto the distal end of the femur via the shaft by means of the handgrip and at the moment when the transverse force components are minimized can lock it by means of the actuating element. Fixation is triggered by actuating the actuating element that thus remains unactuated for the period during which the shaft is positioned. Alternatively, fixation can be a standard adjustment that is triggered by actuating the actuating element for the positioning period. Fixation occurs automatically if the actuating element is then for example released.

An inventive apparatus is perceived as particularly ergonomic and advantageous when the handgrip and shaft, especially also the actuating element in the handgrip, are formed like a pistol. Then an operator can take the inventive apparatus in the hand in the manner of a pistol and exert the measuring force onto the distal end of the femur. This can be triggered by one or a plurality of fingers on the hand operating the above-described actuating element in order to fix the shaft in its position.

In order to create the lockable, angle-variable, especially swiveling, connection between shaft and mount that is cited above, this connection is a ball-and-socket joint. This has the special advantage that because of this there can be a swiveling connection in two dimensions, especially within a spherical region about the center of the sphere. Thus there are numerous positioning options for the operator within the sphere provided by the apparatus, the sphere limiting all possible positions of the shaft within the mount.

In this case, locking the ball-and-socket connection can occur for instance in that the sphere is prestressed against a spherical shell-like element by a spring and this spring pretension is reduced for instance while the apparatus is positioned in the ideal position and then, when locking is desired, this reduction is eliminated. This can result in a press fit between the sphere and a spherical shell in which the sphere is seated. The shaft can be adequately fixed by the resultant friction.

The force/torque sensor that is employed here can preferably be created as a separate component that, as cited above, can be detachably arranged between handgrip and shaft. The force/torque sensor can for instance have a first ring that is joined via at least three bars to a second ring arranged coaxially therein, each bar having at least one force sensor, in particular a strain gauge.

Thus signals can be electronically captured on the strain gauges that are provided on the bars, these signals representing forces acting between the two rings. Thus these signals can be evaluated in order to activate a display as described above so that it is possible for a user to see the magnitude of the transverse force components.

In this case, the first ring is secured to the handgrip and the second ring is joined to the shaft or at least can be connected in a separate component. In particular the embodiment as a separate component has the advantage that the apparatus can be removed and sterilized in its entirety, for instance in an autoclave. Thus it can be inventively provided that the apparatus can be autoclaved in its entirety, or at least its components can be autoclaved.

Due to the annular embodiment of the second ring that is disposed coaxially on the inside, the above-described force/torque sensor has the additional advantage that a pin for actuating the locking apparatus, as cited above, extending through the tubular shaft can pass through this second ring. Thus overall with such a force/torque sensor and the inventive apparatus it is possible to ensure that the direction of the force exerted always runs centrally through the measuring apparatus.

A force/torque sensor can also be constructed in any manner, for example even purely mechanically without electronics.

One embodiment of the invention is shown in the following figures.

Figure 3:
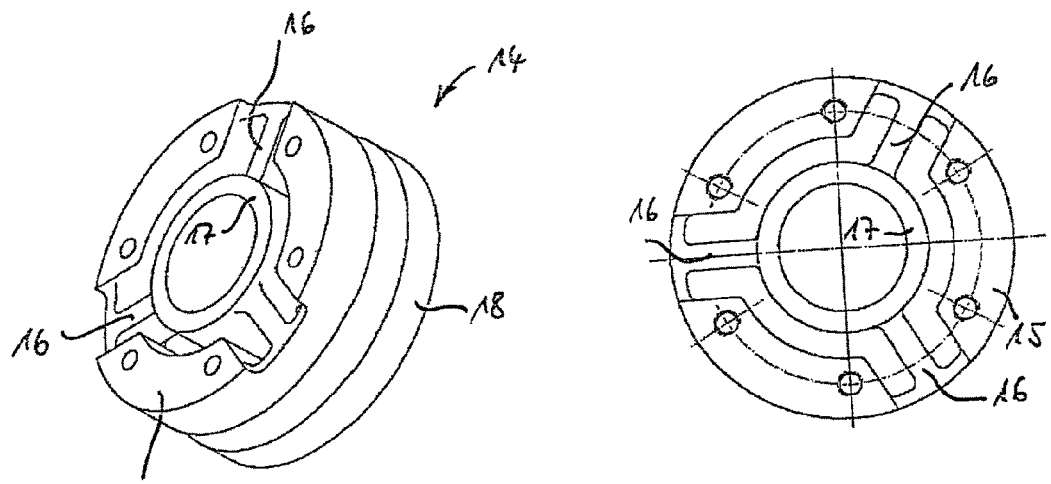
Figure 2:
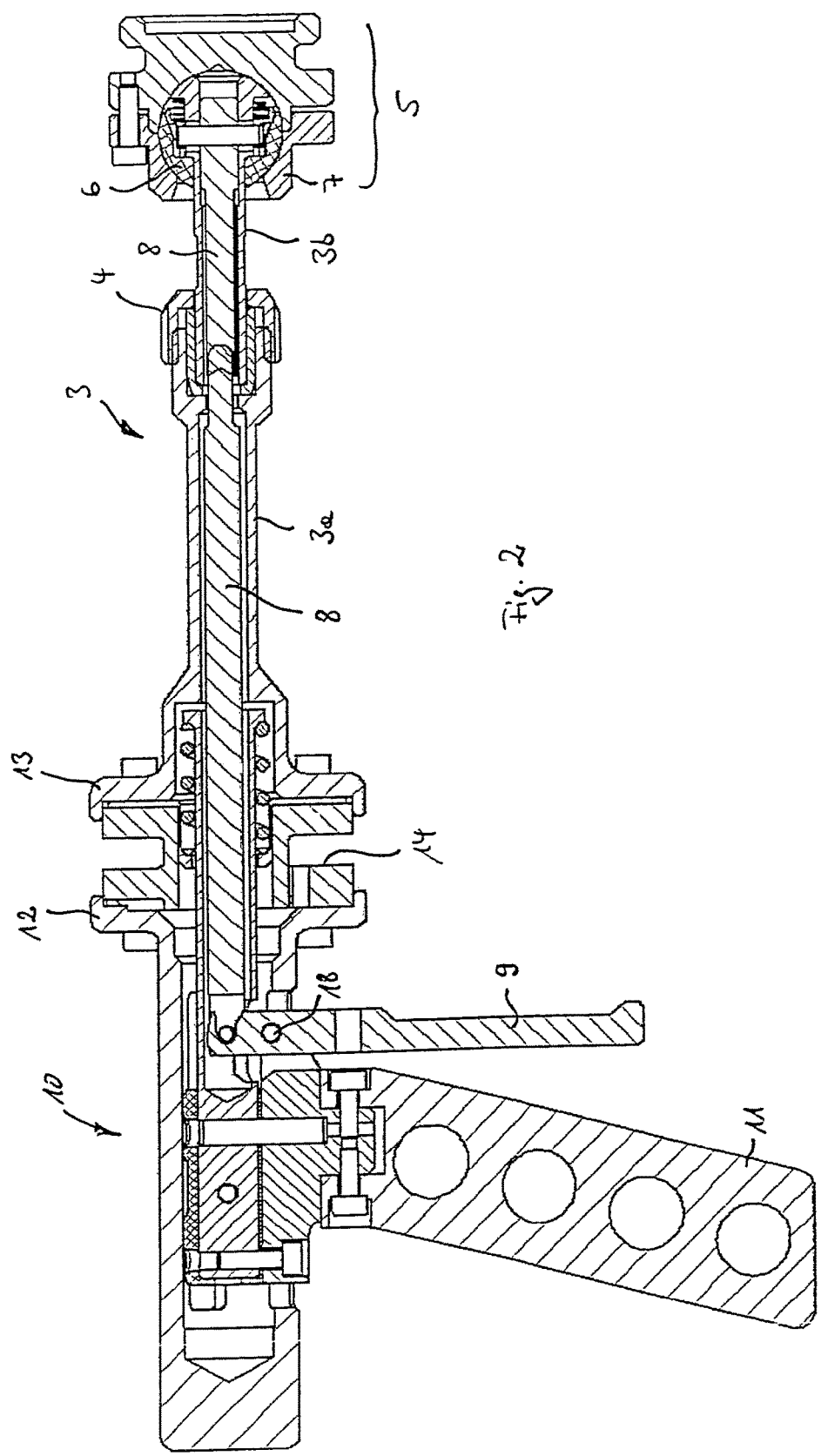
Figure 4:
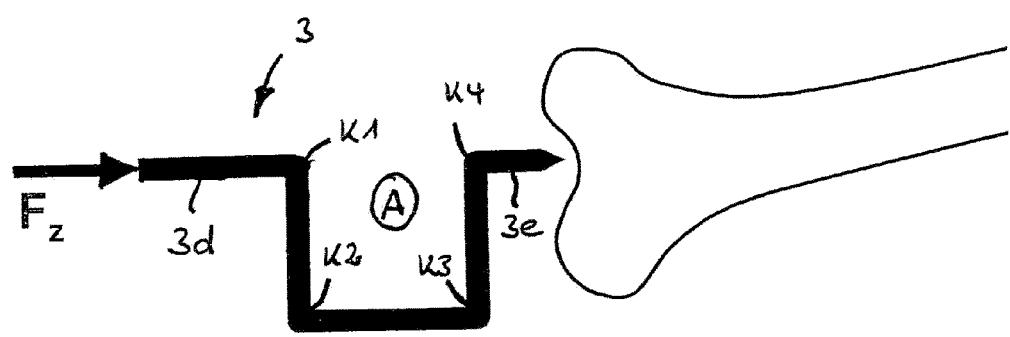
Figure 5:
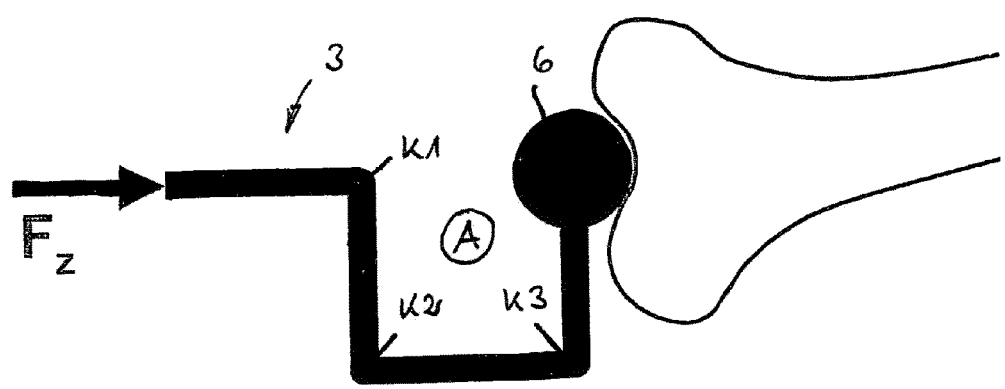

FIG. 1 shows the force situation when employing the inventive method and apparatus;
FIG. 2 is a cross-sectional view of an inventive apparatus;
FIG. 3 are two elevational views of a force-sensor;
FIG. 4 shows a first embodiment of a shaft with bends to fit around a knee-cap;
FIG. 5 shows a second embodiment of a shaft with bends to fit around a knee-cap.

FIG. 1 provides a schematic view of a femur 1 to whose distal end 1a a knee prosthesis is to be attached. It can be seen here that the connecting line 2, the so-called Mikulicz line or the mechanical axis of the femur 1 that connects the knee joint 1b to the femoral head 1c, passes outside the longitudinal extension of the bone 1.

The object of the invention is to find this ideal line 2 with the inventive method or the inventive apparatus, to which end a force FZ is exerted on the knee joint 1b by means of the inventive apparatus via a shaft 3 in a direction Z, assumed in this case, for which purpose the end of the shaft 3 is secured to the knee joint 1b by means of a mount and the end of the shaft 3 can swivel in this mount.

Thus if the force FZ is exerted at a rear end of the shaft 3, for example via a handgrip, onto the knee joint 1b, the active force is split into two components X and Y if the direction of the force FZ does not coincide precisely with the Mikulicz line 2. This results in measurable torques at the site of the force/torque sensor. In accordance with the invention these force components and/or the torques generated by them are detected and displayed. Then, when these force components/torques are minimized or ideally are zero, one can be sure that the direction of the force FZ coincides with the Mikulicz line 2 and thus the orientation of the shaft 3 is ideal for subsequent surgery. The position of the shaft 3 can then be fixed inventively.

FIG. 2 is a sectional view of an inventive apparatus that can be used for carrying out the method. This FIG. 2 shows an apparatus designed in like a pistol and having a shaft 3 that is divided into two parts 3a and 3b. Part 3b is connected to part 3a via a connector 4 that can be of the a screw-on type.

Furthermore, the part 3b can swivel on a mount 5 that can be at least temporarily fixed to the knee joint. In this swivel shown here the right-hand end of the shaft 3b is connected to an at least partially spherical ball element 6, that can swivel in a spherical shell 7 that itself is carried on the mount. The ball 6 is pretensioned or loaded to the left by springs so that the ball 6 is pressed against the spherical shell 7 by this spring force and thus is fixed in its position.

FIG. 2 shows that the shaft 3 is tubular with a pin 8 divided in two at a connector 4 and that passes through the shaft. The pin 8 can be moved axially in the shaft 3 by an actuating lever 9 carried on a handgrip 10, so that pulling the lever 9 toward the grip 11 advances the pin 8 to the right and thus either reduces the spring tension on the ball 6 or, in another unillustrated embodiment, presses the ball out of the spherical shell and thus frees the shaft in its movement about the ball's center.

Between the handgrip 10 and the shaft 3 here between two flanges 12 and 13 is a force/torque sensor 14 shown in greater detail in FIG. 3. The total actual force that is exerted on the distal end of the femur by the handgrip 10 and the shaft 3 can be detected by means of this force/torque sensor 14, as can transverse force components, especially those that are perpendicular to the direction of the exerted force, as well as torques generated in this manner at the site of the force/torque sensor.

FIG. 3 shows two different views of a force/torque sensor 14 in accordance with the invention. This force/torque sensor includes a first ring 15 that can be connected to one of the flanges 12 or 13 and that is here connected to an inner ring 17 by three bars 16. This inner ring 17 that is coaxial with the first ring 15 merges with another ring 18 that has essentially the same diameter as the first ring 15. This additional ring 18 can be connected to the other flange, i.e. one of the two flanges 12 or 13, so that the force sensor shown here can be arranged between the handgrip 10 and the shaft 3 as shown in FIG. 2. The pin 8 shown in FIG. 2 can here pass through the inner free area of the ring 17.

In this embodiment, strain gauges for instance can be provided on the bars 16 so that in a preferred embodiment at least two strain gauges are employed per bar (on different faces of the bar). The above-described transverse force components can be electronically detected and evaluated using these strain gauges. The output signals can be supplied for instance to a display. The displayed output signals, for example in the form of cross-hairs, could then constitute an aid to assist an operator to position the shaft 3 along the Mikulicz line, which occurs when the transverse components are minimized or equal to zero.

With regard to FIG. 2, the shaft 3 or at least its right-hand end part 3b is fixed in the mount 5 when the grip 9 is released, i.e. as shown in FIG. 2, when it is spaced from the handle 11. The trigger 9 can pivot about an axis 19 on the handgrip so that its upper end moves to the left when it is released and thus the pin 8 is also pushed to the left inside the shaft 3. This means that the spring pretension is again acting completely on the ball 6 within the mount and thus presses it against the spherical shell 7, fixing it in position.

When the position of the shaft 3 is fixed precisely enough, the connector 4 between the two parts 3a and 3b of the shaft 3 can be disconnected so that only the fixed part 3b remains on the distal end of the femur. This remaining part 3b of the shaft can then be used as a mounting pin for fitting a knee prosthesis in a subsequent surgical procedure.

FIG. 4 shows an embodiment in which the shaft has a plurality of bends K1, K2, K3, and K4 in its end near the mount. The shaft segments 3d and 3e that are upstream and downstream of the bends are in a line and are aligned. The bends define a recess that can accommodate a knee cap so that the shaft surrounds it.

FIG. 5 shows an alternative embodiment in which the last bend 4 from FIG. 4 is missing and after the third bend K3 the shaft 3 transitions directly into a ball 6 that can swivel in the mount.

With respect to all embodiments, the technical features cited in connection with one embodiment can be used not only in that specific embodiment, but also in any of the other embodiments. All disclosed technical features of this description of the invention shall be construed to be essential to the invention and combinable with one another in any desired fashion or employable by is themselves.

The invention claimed is:

1. An apparatus for determining the mechanical axis of a bone having an exposed distal end, the apparatus comprising:
   a mount fixable on the distal end of the bone;
   an elongated shaft having inner and outer ends;
   a lockable ball-and-socket joint between the inner end of the shaft and the mount, whereby the shaft can swivel relative to the mount around and through a position aligned with the mechanical axis of the bone;
   a handgrip on the outer end of the shaft for exerting an axial force along an axis of the shaft on the joint and therethrough on the distal end of the bone; and
   force/torque sensor means between the handgrip and the shaft for detecting transverse forces resulting from exerting of the axial force by the shaft on the bone.

2. The apparatus in accordance with claim 1 wherein the force/torque sensor means is detachably mounted between the handgrip and the shaft.

3. The apparatus in accordance with claim 1 wherein the force/torque sensor means is a mechanical apparatus for displaying torques or longitudinal forces.

4. The apparatus in accordance with claim 1 wherein parts of the apparatus can be autoclaved.

5. An apparatus for determining the mechanical axis of a bone having an exposed distal end, the apparatus comprising:
   a mount fixable on the distal end of the bone;
   an elongated tubular shaft having inner and outer ends;
   locking means for locking in position the swivel joint, the locking means being releasable or operable through the tubular shaft;
   a swivel joint between the inner end of the shaft and the mount, whereby the shaft can swivel relative to the mount around and through a position aligned with the mechanical axis of the bone;
   a handgrip on the outer end of the shaft for exerting an axial force along an axis of the shaft on the swivel joint and therethrough on the distal end of the bone; and
   force/torque sensor means between the handgrip and the shaft for detecting transverse forces resulting from exerting of the axial force by the shaft on the bone.

6. The apparatus in accordance with claim 5 wherein inside the tubular shaft is a pin by means of which the locking apparatus can be actuated in the mount.

7. The apparatus in accordance with claim 6 wherein the pin can be actuated using an actuating element on the handgrip.

8. The apparatus in accordance with claim 6 wherein the force/torque sensor means is formed as a first ring joined via at least three bars to a second ring arranged coaxially therein, each bar having at least one strain gauge.

9. The apparatus in accordance with claim 8 wherein the first ring is connectable to the handgrip and the second ring is connectable to the shaft.

10. The apparatus in accordance with claim 8 wherein the pin passes through second ring for actuating the locking apparatus.

11. An apparatus for determining the mechanical axis of a bone having an exposed distal end, the apparatus comprising:
    a mount fixable on the distal end of the bone;
    an elongated shaft having inner and outer ends and at least two parts, one part being connected to the mount and the other part having the force/torque sensor means and both parts being detachably connectable to one another;
    a swivel joint between the inner end of the shaft and the mount, whereby the shaft can swivel relative to the mount around and through a position aligned with the mechanical axis of the bone;
    a handgrip on the outer end of the shaft for exerting an axial force along an axis of the shaft on the swivel joint and therethrough on the distal end of the bone; and
    force/torque sensor means between the handgrip and the shaft for detecting transverse forces resulting from exerting of the axial force by the shaft on the bone.

12. An apparatus for determining the mechanical axis of a bone having an exposed distal end, the apparatus comprising:
    a mount fixable on the distal end of the bone;
    an elongated shaft having inner and outer ends and formed with bends outward of the mount such that the shaft fits around an obstacle at the bends;
    a swivel joint between the inner end of the shaft and the mount, whereby the shaft can swivel relative to the mount around and through a position aligned with the mechanical axis of the bone;
    a handgrip on the outer end of the shaft for exerting an axial force along an axis of the shaft on the swivel joint and therethrough on the distal end of the bone; and force/torque sensor means between the handgrip and the shaft for detecting transverse forces resulting from exerting of the axial force by the shaft on the bone.

13. An apparatus for determining the mechanical axis of a bone having an exposed distal end, the apparatus comprising:
a mount fixable on the distal end of the bone;
an elongated shaft having inner and outer ends;
a swivel joint between the inner end of the shaft and the mount, whereby the shaft can swivel relative to the mount around and through a position aligned with the mechanical axis of the bone;
a handgrip on the outer end of the shaft for exerting an axial force along an axis of the shaft on the swivel joint and therethrough on the distal end of the bone, the handgrip and the shaft being formed like a pistol; and
force/torque sensor means between the handgrip and the shaft for detecting transverse forces resulting from exerting of the axial force by the shaft on the bone.

14. A method for determining the mechanical axis of a femur wherein a shaft is at its one end swivelable but fixable on a mount secured to a distal end of a femur, in particular at the knee joint and that a force can be exerted by the shaft on the distal end so that by means of a torque/force sensor on the shaft forces transverse to the exerted force and/or resultant moments can be measured and the shaft can be fixed in its position by locking the swivel joint when the measured transverse components or their resultant moments are minimized, in particular at zero.

15. The method in accordance with claim 14 wherein the transverse forces/torques are detected electronically and fed to a display.

16. The method in accordance with claim 14 wherein the magnitude of the force exerted is shown on a display in relation to a minimum force.

17. The method in accordance with claim 14 wherein the weight of a femur is determined prior to force being exerted on it.

18. A method of determining the mechanical axis of a bone having an exposed distal end, the method comprising the steps of:
fixing a swivel joint on the distal end of the bone;
securing an inner end of an elongated shaft to the joint such that the shaft can swivel relative to the mount around and through a position aligned with the mechanical axis of the bone;
exerting an axial force against an outer end of the shaft along an axis of the shaft on the swivel joint and therethrough on the distal end of the bone;
detecting transverse forces resulting from the axial force by the shaft on the bone;
orienting at least the inner end of the shaft in a position in which the detected transverse forces are minimized, whereby this position corresponds to alignment of the inner end of the shaft with the mechanical axis;
locking the inner shaft end in the position; and
using the locked inner shaft end to orient a prosthetic joint component on the distal end.

19. The method defined in claim 18, further comprising the step of:
displaying the detected forces.

* * * * *